US00PP07973P

United States Patent [19]

Twomey

[11] Patent Number: Plant 7,973

[45] Date of Patent: Sep. 15, 1992

[54] HYBRID TEA ROSE PLANT NAMED TWOADMIRE

[75] Inventor: Jerry Twomey, Leucadia, Calif.

[73] Assignee: DeVor Nurseries, Inc., Watsonville, Calif.

[21] Appl. No.: 627,037

[22] Filed: Dec. 13, 1990

[51] Int. Cl.[5] ..... A01H 5/00

[52] U.S. Cl. ..... Plt./21

[58] Field of Search ..... Plt./20, 21

*Primary Examiner*—Howard J. Locker

*Attorney, Agent, or Firm*—Christie, Parker & Hale

[57] ABSTRACT

A new hybrid tea rose plant producing red flowers.

1 Drawing Sheet

SUMMARY OF THE INVENTION

The present invention relates to a new and distinct variety of rose plant of the hybrid tea rose class which was originated by my crossing as seed parent the variety known as 'Portland Trailblazer' (U.S. Plant Pat. No. 4,222) and as pollen parent an unnamed and unpatented seedling of my creation. The varietal denomination of this new rose is 'Twoadmire'.

Among the novel characteristics possessed by this new variety which distinguishes it from its parents and all other varieties of which I am aware are its attractive well formed red flowers borne on a plant particularly suitable for use in gardens. Flowers open well and hold their coloring as blooms age. The new variety is also characterized by its health, vigor and flower production.

Asexual reproduction by budding and rooting of cuttings of the new variety as performed in Glenn County, Calif. and Kern County, Calif., shows that the foregoing and other distinguishing characteristics come true to form and are established and transmitted through succeeding propagations.

BRIEF DESCRIPTION OF ILLUSTRATIONS

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

Twoadmire is an unusually fine hybrid tea rose of red flower coloration. It is especially well suited for growing outdoor in gardens. The variety blooms freely under natural growing conditions. The foliage is dark green, and semi leathery.

The following is a detailed description of my new variety, with color terminology in accordance with the Royal Horticultural Society Color Chart (R.H.S.C.C.). The terminology used in color description herein refers to plate numbers in the aforementioned color chart.

Parentage: Seedling.

*Seed parent.*—'Portland Trailblazer'.

*Pollen parent.*—Unnamed seedling.

Class: Hybrid tea.

The following information is from observations made of specimens grown outdoors in Watsonville, Calif.

FLOWER

Blooming habit: Continuous.

A. Bud:

(1) *Size.*—Medium; about 2-cm in diameter and 2.5-3 cm in length.

(2) *Form.*—Slightly pointed.

(3) *Color.*—As sepals divide, bud color is near 185A.

(4) *Sepals.*—5 to 6; longer than bud; simple to foliaceous. Color: Inside — near 147C with near 196D hairs covering surface Outside — near 144B at base and tip and near 178B on remainder.

(5) *Peduncle.*—Length: 6.5 cm to 7 cm; small spines. Aspect: Straight. Strength: Erect, rigid. Color: Near 183A.

(6) *Calyx.*—Shape: Funnel shaped; does not split. Size: Medium; 1.1 cm×1 cm.

B. Bloom:

(1) *Size.*—Average size when fully expanded — about 10 cm; depth about 3.5 cm.

(2) *Borne.*—Singly, one to a stem, disbudded.

(3) *Form.*—Cupped.

(4) *Petalage.*—Number of petals under normal conditions — about 25 to 28.

(5) *Color.*—After sepals fall and petals unfurl, predomiant flower color viewing petals' top surface is near 46A to 45A. Color is general and substantially constant though with darker hues sometimes at petal edges. Petal undersurface displays similar coloration. Color at point of petal attachment is near 1C.

C. Petals:

(1) *Texture.*—Medium to thick.

(2) *Appearance.*—Inside velvety and outside satiny.

(3) *form.*—Broad, fan shaped with some indentation or undulation at margin (slightly lobed).

(4) *Arrangement.*—Regularly arranged, imbricated.

(5) *Fragrance.*—Moderate musk.

(6) *Lasting quality.*—Long lasting on plant and as cut flower.

REPRODUCTION ORGANS

A. Stamens:

*Number.*—Approximately 180.

*Arrangement.*—Slightly introrse.

*Anthers.*—Size — 0.3 cm. Color — near 163A.

*Filaments.*—(Threads): Length — 0.5 to 0.8 cm. Color — near 179A. Pollen: Color — near 167A.

B. Pistils:

*Number.*—Approximately 178.

*Styles.*—Length — 1 cm. Color — near 185B at tip with near 145D on remainder.

*Stigmas.*—Color — near 160D.

C. Characteristics of ovaries: Small, oblong with silvery hairs.

D. Hips:

*Fertile.*—Yes.

*Shape.*—Round.

*Color at maturity.*—Near 31B.

PLANT

A. Form: Well shaped, symmetrical.

B. Growth: Vigorous, upright; free branching; height attained about 105 cm at three years.

C. Foliage: Compound 3, 5 and 7 leaflets.

(1) *Size.*—About 18 cm×15 cm.

(2) *Quantity.*—Abundant.

(3) *Color.*—Upper side — dark green. Under side — light green.

(4) *Shape.*—Oval, pointed.

(5) *Texture.*—Semi-leathery; upper side is glossy, under side is matte.

(6) *Edge.*—Serrate, (denticulate).

(7) *Serration.*—Ordinary.

(8) *Leaf stem.*—Color — medium green.

(9) *Stipules.*—Hairy, adnate with some glands.

(10) *Tetiolule.*—About 0.2 cm.

(11) *Rachis.*—About 8.5 cm on 3 leaf; 14.5 cm on 7 leaf.

(12) *Petioles.*—Length — 0.5 cm on 3 leaf; 2 cm on 7 leaf.

(13) *Ribs and veins.*—Both slightly depressed on top and rounded underneath. Rachis: Occasional small spines underneath.

(14) *Resistance to disease.*—Moderately resistant to mildew, rust and black spot.

D. Wood (1) *New wood.*—Color — purple/red. Bark — smooth.

(2) *Old wood.*—Color — purple/red. Bark — smooth.

E. Thorns:

*Quantity (main stalk).*—Average.

*On laterals from stalk.*—Average.

*form.*—Thin, straight, angled downward.

*Length.*—Medium.

*Color.*—Near 174A.

*Position.*—Irregular.

*Prickles:* Few to none present.

F. Winter hardiness: Needs protection in severe climates.

I claim:

1. A new and distinct variety of rose plant of the hybrid tea rose class, substantially as shown and described.

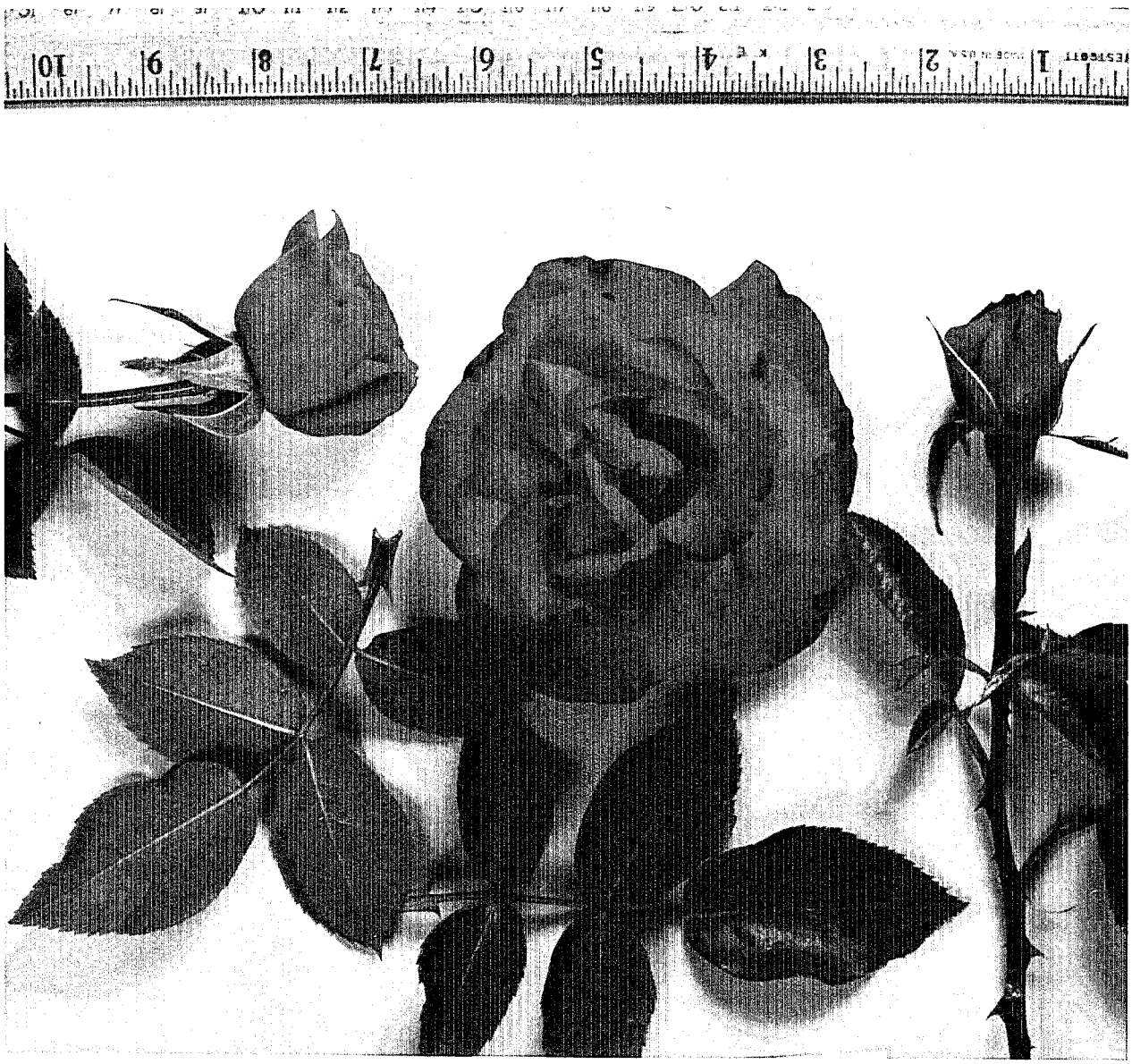

* * * * *